United States Patent [19]

Dedinas

[11] 4,168,218
[45] Sep. 18, 1979

[54] PREPARATION OF SUBSTITUTED BENZOPINACOLS

[75] Inventor: Jonas Dedinas, Pittsford, N.Y.

[73] Assignee: Eastman Kodak Company, Rochester, N.Y.

[21] Appl. No.: 877,452

[22] Filed: Feb. 13, 1978

Related U.S. Application Data

[63] Continuation-in-part of Ser. No. 799,798, May 23, 1977, abandoned.

[51] Int. Cl.$^2$ .............................................. B01J 1/10
[52] U.S. Cl. .............................. 204/158 R; 568/638; 568/633; 568/637; 568/719; 568/718; 568/640; 568/641
[58] Field of Search ........... 260/619 B, 613 R, 618 B; 204/158 R

[56] References Cited

U.S. PATENT DOCUMENTS

3,497,430  2/1970  French et al. ........................ 204/77

OTHER PUBLICATIONS

Filler et al., J. Org. Chem., vol. 40, No. 8, 1975, pp. 1173 to 1175.
Dedinas, J. Am. Chem. Soc., vol. 95, No. 21, pp. 7172 to 7174 (1973).
Schonberg, Preparative Organic Photochemistry, Springer-Verlag, N.Y., N.Y., (1968), pp. 203 to 209.
Dedinas et al., J. Phys. Chem., vol. 76, No. 26, 1972, pp. 3926 to 3933.
Research Disclosure, Oct. 1973, pp. 12 to 13, Item 11409 of DeSelms.

*Primary Examiner*—Leland A. Sebastian
*Attorney, Agent, or Firm*—Richard E. Knapp

[57] ABSTRACT

Benzopinacol compounds can be prepared by an improved process comprising irradiating a diarylketone with UV radiation in a non-polar hydrocarbon solvent mixed with an alcohol. The volume ratio of the non-polar hydrocarbon solvent to alcohol is between 3:1 and 8:1. The benzopinacols are useful, for example, in imaging materials, such as with certain dyes that are reactive with the ketyl radicals that can be released from the benzopinacols upon heating.

10 Claims, No Drawings

PREPARATION OF SUBSTITUTED BENZOPINACOLS

This is a continuation-in-part application of U.S. Ser. No. 799,798 of Jonas Dedinas, filed May 23, 1977, now abandoned.

BACKGROUND OF THE INVENTION

1. Field of the Invention

The present invention relates to a new process for preparing benzopinacols. In one aspect the invention relates to preparation of p-hydroxy, p-alkoxy or p-phenoxy substituted benzopinacols containing at least 8 fluorine substituents.

2. Description of the State of the Art

Several fluorine substituted benzopinacols are known in the art. Filler and Kang, in *J. Organic Chemistry*, Vol. 40, No. 8, pages 1173 (1975), describe the preparation of a decafluorobenzopinacol by the photochemical bimolecular reduction of pentafluorobenzophenone in a 40:1 solution of n-hexane/2-propanol. While this reaction is suitable for some benzopinacols, it is not possible to produce many benzopinacols, such as perfluorobenzopinacol. Filler and Kang attempted this preparation and failed. Furthermore, the yield from this method is generally low, for example, being no higher than 65% for the production of decafluorobenzopinacol. The general method for the preparation of a benzopinacol by photochemical means is described in A. Schönberg, "Preparative Organic Photochemistry," Springer-Verlag, N.Y., N.Y., beginning at page 203, (1968). Schonberg also describes certain 4-methoxybenzopinacols; however, none of these are also fluorine substituted. No utility for these benzopinacols is described in these references.

In "Solvent Effect in the Photoreduction of Decafluorobenzophenone by 2-Propanol," by J. Dedinas, *Journal of the American Chemical Society*, 95:21, pages 7172 (1973), the preparation of perfluorobenzopinacol, also known as eicosafluorobenzopinacol, is described as the photochemical reaction of decafluorobenzophenone with 2-propanol. The solvent used was perfluoromethylcyclohexane which was less than 0.04 molar in 2-propanol. While the perfluoroalkane solvent is useful, it is comparatively expensive, making it impractical to use in large scale operations. Further, the diarylketone starting material is frequently only marginally soluble in perfluoroalkane solvents. This means that large quantities of these expensive solvents must be used for reasonable throughputs.

Preparations of other benzopinacols are known. These are described, for example, in the following: M. Gomberg and W. E. Bachman, *J. of American Chemical Society*, Vol. 49, pages 236–257; U.S. Pat. No. 2,306,338 of Hester, issued Dec. 22, 1942; and U.S. Pat. No. 3,497,430 of French et al, issued Feb. 24, 1970. None of the described preparations provide answers to the problems in preparation of a benzopinacol containing at least 8 fluorine substituents. None of the benzopinacols described contain at least 8 fluorine substituents.

In *Research Disclosure*, Vol. 161, September 1977, Item No. 16160, of Jonas Dedinas and George L. Fletcher, Jr. the use of benzopinacols is described in imaging materials, such as photographic elements. In these applications benzopinacols are useful as ketyl radical release agents.

Benzopinacols are also described in *Research Disclosure*, October 1973, pages 12–13, published by Industrial Opportunities Ltd., Homewell, Havant Hampshire, PO9 1EF, UK.

The ketyl radicals can cause the reduction of a dye and as such can be used in a variety of imaging applications. For example, the benzopinacol and a dye are useful together in an antihalation layer for a photothermographic element. This is described in the *Research Disclosure Item* No. 16160, of Fletcher and Dedinas. Processing of the photothermographic element by heat releases the ketyl radicals from the benzopinacol and reduces the dye in the antihalation layer. Thus, the color of the dye is present in the antihalation layer when it is needed during exposure and is removed by the heat generated ketyl radical from the benzopinacol during processing.

The requirements for chemicals used in photographic elements are stringent and while benzopinacols in general are useful in photographic elements for processing with heat, known benzopinacols do not provide all of the properties that are desirable for many photographic elements. For example, one of the known substituted benzopinacols, decafluorobenzopinacol, can be used in heat developable photographic elements, such as in combination with certain dyes in a heat bleachable antihalation layer. The layer containing the decafluorobenzopinacol is stable with good keeping characteristics. Unfortunately, upon heating, decafluorobenzopinacol and other known substituted benzopinacols release ketyl radicals which have less than desired activity and do not easily reduce some dyes to the desired degree. As a practical matter, this means that either excessive amounts of known benzopinacols must be used or alternatively, the choice of dyes for a photographic element is greatly narrowed. The prior art does not suggest how the activity of the ketyl radicals that are released from the known benzopinacol might be increased while retaining the other desirable characteristics of the benzopinacols.

There has been a need to provide new fluorine substituted benzopinacols that provide improved ketyl radical release properties for imaging materials. There has also been a need to provide an improved process of preparing benzopinacols, especially fluorine substituted benzopinacols that provide improved yields without large quantities of expensive solvents.

SUMMARY OF THE INVENTION

An improved process has been found according to the invention for preparing benzopinacols. The process comprises irradiating, with UV radiation, at least one appropriate aromatic ketone in a non-polar hydrocarbon solvent mixed with an alcohol. In the process the solution containing the aromatic ketone is neutral or acidic. Also, the volume ratio of the non-polar hydrocarbon solvent to alcohol is between 3:1 and 8:1.

A preferred embodiment of the process comprises the steps of, respectively:

(a) preparing a 0.005 to 1.0, preferably 0.01 to 0.5, molar neutral or acidic solution of at least one aromatic ketone in a solvent having a boiling point less than about 120° C. and comprising a mixture of a non-polar hydrocarbon and an alcohol wherein the volume ratio of the non-polar hydrocarbon to the alcohol is between 3:1 and 8:1; (b) irradiating the solution with ultraviolet light at an intensity and for a time sufficient to effect conversion of the aromatic ketone to the desired benzopinacol; and (c) removing the solvent mixture from said solution at a temperature sufficient to reduce the rate of the benzopinacol decomposition, preferably to insignificant levels. For example, temperatures less than 40° C. have been very useful in preventing or reducing such decomposition. It was found that this process is unexpectedly applicable to benzopinacols in general and produces the desired bnzopinacol product in unexpectedly high yield.

It has been found that the described process according to the invention can be especially useful for preparing certain fluorine substituted benzopinacols which provide unexpectedly improved activity in heat developable photographic elements while retaining the desirable characteristics of ease of processing and excellent stability. The described process is useful for preparing new fluorine substituted compounds represented by the formula:

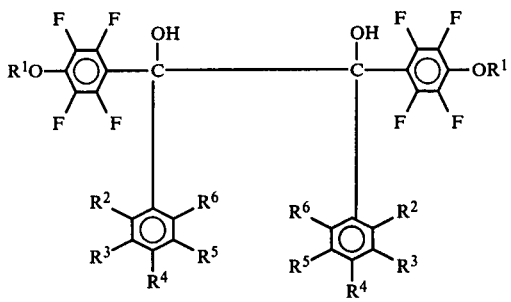

wherein
- $R^1$ is hydrogen, alkyl including cycloalkyl, such as alkyl containing 1 to 16 carbon atoms, typically 1 to 6 carbon atoms, including methyl, ethyl, propyl and cyclohexyl, including substituted alkyl, or aryl, such as aryl containing 1 to 16 carbon atoms, including phenyl and biphenylyl, including substituted aryl, such as methoxyphenyl, methylphenyl and the like;
- $R^2$ and $R^6$ independently are selected from the group consisting of hydrogen, halogen and trifluoromethyl;
- $R^3$ and $R^5$ independently are selected from the group consisting of hydrogen, halogen and alkyl including cycloalkyl, such as alkyl containing 1 to 16 carbon atoms, typically 1 to 6 carbon atoms, including methyl, ethyl, propyl and cyclohexyl, including substituted alkyl, or when taken together with $R^4$ represent a tetramethylene group; and
- $R^4$ is selected from the group consisting of hydrogen, halogen, alkyl, such as alkyl containing 1 to 16 carbon atoms, typically 1 to 6 carbon atoms, including methyl, ethyl and propyl, including cycloalkyl, e.g., cyclohexyl and substituted alkyl; alkoxy, such as alkoxy containing 1 to 16 carbon atoms, including methoxy, ethoxy and cyclohexyloxy; and phenoxy, including substituted alkoxy and phenoxy such as methoxyphenoxy, methylphenoxy and the like;
- with the proviso that when both of the ortho positions of the phenyl groups to which $R^2$ and $R^6$ are attached are substituted, the substituent is fluorine.

The compounds have improved activity as ketyl radical release agents compared to known benzopinacols. Particularly preferred compounds of the present invention are those wherein $R^2$ and $R^6$ are hydrogen or wherein one of $R^2$ through $R^6$ is fluorine and the remainder of $R^2$ through $R^6$ are hydrogen. These preferred compounds have all of the advantages of other compounds within the invention and, in addition, have even better preprocess keeping properties in imaging elements.

DETAILED DESCRIPTION OF THE INVENTION

Benzopinacols according to the invention are made by the photoreduction of the corresponding diarylketone in the presence of an alcohol such as isopropanol or ethanol. The corresponding diarylketone can be prepared by means of Friedel-Craft alkylation of the corresponding benzene with the proper fluorine substituted benzoyl chloride using $AlCl_3$. The reaction can be carried out in a carbon disulfide solvent or in an excess of the corresponding substituted benzene. Another method of producing the necessary diarylketone is by nucleophilic displacement of halogen in a halogen substituted benzophenone. Preferably, the halogen substituent to be replaced is fluorine since fluorine is known to undergo nucleophilic substitution with greater ease than other halogens. The p-fluorine is easily replaced by alkoxy or phenoxy groups using a salt of the replacing group. As examples, 4-methoxy-2,3,5,6-tetrafluorobenzophenone is made by reacting 2,3,4,5,6-pentafluorobenzophenone with $NaOCH_3$ in methanol; and 4-(4-methoxyphenoxy)-2,3,5,6-tetrafluorobenzophenone is made by reacting 2,3,4,5,6-pentafluorobenzophenone with 4-methoxyphenol and NaOH. Other substituted benzophenones are similarly made.

Benzopinacols, as described, are made in solvent mixtures. The described substituted benzopinacols undergo decomposition in solution, the rate of decomposition being dependent on the type of solvent used. In polar solvents the rate of decomposition is much greater than in non-polar solvents. Since the alcohols, which are used to provide the hydrogen necessary in the photoreduction of the benzophenones, are polar solvents, the use of pure alcohol would substantially diminish the yield of the substituted benzopinacol. For some benzopinacols, the synthesis in pure alcohol is not possible at all. Conversely, using a pure hydrocarbon solvent with a minor amount of alcohol is often unsatisfactory. Frequently, the reaction does not lead to the desired benzopinacol, but to aromatic-ring substituted products and tertiary alcohols. In some cases use of a substantial portion of inert hydrocarbon solvent results in large quantities of these undesirable byproducts, thereby diminishing the yield of the desired benzopinacol.

It has been found that a solvent mixture having a non-polar hydrocarbon solvent to alcohol ratio of between about 3:1 and about 8:1, provides the desired high yields of substituted benzopinacols.

In the preparation of benzopinacols described herein, the diarylketone is excited by light to its reactive $^3(n, \pi^*)$ state. The reactivity of decafluorobenzophenone in this state is described in T. A. Regan and J. Dedinas, "Kinetics and Mechanism of Decafluorobenzophenone Photochemical Reactions in Cyclohexane, Benzene and Alkyl Aromatics," *Journal of Physical Chemistry*, Vol. 76, No. 26, page 3926 (1972). While the reaction can be carried out in other solvents, it is preferred that the non-polar hydrocarbon solvent be chosen so that the $^3(n, \pi^*)$ state of the diarylketone is not excessively quenched. Aromatic solvents quench the $^3(n, \pi^*)$ state of the ketones thereby substantially reducing the quantum yield and requiring excessively long reaction times. As a result, alkane non-polar solvents are preferred. Similarly, oxygen quenches the $^3(n, \pi^*)$ state of the ketones and thus it is desirable to deoxygenate the reaction solution in order to increase the quantum yield and decrease the required reaction time. Bubbling an inert gas, such as nitrogen, through the reaction solution is a suitable method of deoxygenating the solution.

Other factors for selection of a suitable non-polar hydrocarbon solvent are its boiling point and the solubility of the ketone. Since the benzopinacol product is heat sensitive, it is desirable to use a non-polar hydrocarbon solvent with a relatively low boiling point. When such a solvent is chosen, the solvent mixture may be easily removed by a vacuum evaporator at a temperature below which the benzopinacol product does not undergo significant decomposition. While in some cases a higher boiling product solvent can be used, it is preferred that the boiling point of the non-polar hydrocarbon solvent be lower than about 120° C. at standard atmospheric pressure. With such a solvent, vacuum evaporation of the solvent mixture at a temperature not exceeding 40° C. is possible. While vacuum evaporation temperatures above 40° C. may be used when the benzopinacol yield need not be optimum, temperatures below 40° C. are preferred in order to maximize yield. The ketone must be adequately soluble in the solvent mixture, so that it should be possible to prepare a 0.001 molar to 1.0 molar solution of the ketone. Once the ketone has been selected, the non-polar hydrocarbon solvent to be used with the alcohol in the mixture can be determined by a simple test. Examples of useful non-polar hydrocarbon solvents include cyclohexane, n-pentane, heptane, and other alkanes. Aromatics such as toluene, benzene and various xylenes can also be useful particularly with ketones which are not sufficiently soluble in alkanes.

A variety of alcohols can be useful in forming the described solvent mixture. The reaction mixture must have a boiling point below about 120° C. Typically this means that the alcohol itself preferably has a boiling point below about 120° C. but where the alcohol forms an azeotrope with the inert organic solvent, it is sufficient that the azeotrope have a boiling point below about 120° C. Useful alcohols include straight and branched chain aliphatic alcohols such as isopropanol, ethanol and the like. Isopropanol is preferred.

The substituted benzopinacols prepared according to the invention are unstable under basic conditions. Base enhances the deprotonation of the benzopinacol and leads to rapid decomposition. As a result, the reaction to prepare these benzopinacols should be carried out under neutral or acidic conditions. In order to insure that the solvent mixture is neutral or acidic, a small amount of an organic acid, such as acetic acid, may be added.

The time required to complete the reaction varies widely depending upon the diarylketone, solvent mixture and light source selected. The extent of conversion can be followed by removing small samples and analyzing for UV absorption in the 330 to 350 nm region. Conversion of the ketone to benzopinacol is complete when essentially no absorption in this region is observed. Typically, irradiation can vary from between 2 to 5 hours at a temperature less than 35° C. such as −20° C. to 35° C., however times and temperatures outside of this range can also be used. A variety of ultraviolet light sources are useful; but, the light source must be of sufficient intensity to provide the desired reaction. The light source can be a mercury or mercury-xenon arc lamp or any other source providing UV radiation. A suitable arrangement includes a 450 watt mercury arc lamp made by Hanovia immersed in 250 ml of the reaction mixture.

Illustrative compounds which can be prepared according to the invention include:

4,4''-dimethoxy-2,3,5,6,2'', 3'', 5'',6''-octafluorobenzopinacol 4,4''-dimethoxy-2,3,5,6,4',2'',3'',5'',6'',4'''-decafluorobenzopinacol 4,4''-bis(4-methylphenoxy)-2,3,5,6,2'',3'',5'',6''-octafluorobenzopinacol 4,4''-bis(4-methoxyphenoxy)-2,3,5,6,2'',3'',5'',6''-octafluorobenzopinacol 4,4''-diphenoxy-2,3,5,6,2'',3'',5'',6''-octafluorobenzopinacol 4,4',4'',4'''-tetramethoxy-2,3,5,6,2',2'',3'',5'',6'',2'''-decafluorobenzopinacol 4,4',4'',4'''-tetramethoxy-2,3,5,6,2'',3'',5'',6''-octafluorobenzopinacol 4',4'''-dimethoxy-4,4''-dicyclohexyl-2',3',5',6',2''',3''',5''',6'''-octafluorobenzopinacol 4',4'''-dimethoxy-4,4''-dichloro-2',3',5',6',2''',3''', 5''',6'''-octafluorobenzopinacol 4',4'''-dimethoxy-2,4,2'',4''-tetrachloro-2',3',5',6',2''',3''',5''',6'''-octafluorobenzopinacol 4,4''-dimethoxy-2,3,5,6,2',4',2'',3'',5'',6'',2''',4'''-dodecafluorobenzopinacol 4',4'''-dimethoxy-4,4''-dimethyl-2',3',5',6',2''',3''',5''',6'''-octafluorobenzopinacol 4',4'''-dimethoxy-4,4'-di(tertiarybutyl)-2',3',5',6',2''',3''',5''',6'''-octafluorobenzopinacol 1,2-bis-β-(5,6,7,8-tetrahydronaphthyl)-1,2-bis(4-methoxy-2,3,5,6-tetrafluorophenyl)ethanediol 4,4''-dimethoxy-3',4',3''',4'''-tetrachloro-2,3,5,6,2'',3'',5'',6''-octafluorobenzopinacol 4,4''-dimethoxy-3',4',3''',4'''-tetramethyl-2,3,5,6,2'',3'',5'',6''-octafluorobenzopinacol 4,4',4'',4'''-tetramethoxyhexadecafluorobenzopinacol.

The following examples are presented for a further understanding of the invention.

EXAMPLE 1

Synthesis of 4,4''-dimethoxy-2,3,5,6,2'',3'',5'',6''-octafluorobenzopinacol

4-Methoxy-2,3,5,6-tetrafluorobenzophenone (3 g) was dissolved in 250 ml of benzene/isopropanol (0.042 M). The ratio of benzene to isopropanol was 4:1. The solution was irradiated by means of a Hanovia, 450-watt, water-cooled, medium pressure, Hg-arc lamp, which was immersed in the solution. Nitrogen was purged through the solution during the time of the 3 hour irradiation. The solution after irradiation was colorless. The solvent was removed using a rotary, vacuum evaporator. The temperature of the water bath of the evaporator was held below 40° C. The white product crystallized during evaporation of the solvent. The product was washed with 10 ml of n-pentane in order to remove polar solvent impurities (isopropanol) and pinacol decomposition products. Then, the slurry was centrifuged and n-pentane decanted. The washing with n-pentane was repeated once more. The product was spread on a watch-glass and was allowed to dry in air. Finally, it was dried in an air-circulating oven for 10 minutes at 50° C. The yield of 4,4''-dimethoxy-2,3,5,6,2'',3'',5'',6''-octafluorobenzopinacol product was 2.6 g or 86.4 percent. The product had a melting point of 135°–140° C. The following compounds were made in a similar manner:

4,4',4''',4''''-tetramethoxy-2,3,5,6,2'',3'',5'',6''-octafluorobenzopinacol liquid 4,4''-bis(4-methylphenoxy)2,3,5,6,2'',3'',5'',6''-octafluorobenzopinacol mp=130°–133° C.

4,4''-bis(4-methoxyphenoxy)-2,3,5,6,2'',3'',5'',6''-octafluorobenzopinacol liquid 4,4''-diphenoxy-2,3,5,6,2'',3'',5'',6''-octafluorobenzopinacol mp=120°–126° C.

4,4',4''',4''''-tetramethoxy-2,3,5,6,2',2'',3'',5'',6'',2'''-decafluorobenzopinacol mp=114°–119° C.

EXAMPLE 2

Use of benzopinacol

Ethyl red (2.0 mg), 1,1'-diethyl-2,4'-cyanine iodide, was dissolved in 2.0 ml. of acetone/2-methoxyethanol. Then, 50 mg of 4,4''-dimethoxy-2,3,5,6,2'',3'',5'',6''-octafluorobenzopinacol was added. The solution was mixed with 1.0 ml of 20 percent polysulfonamide polymer solution (acetone/2-methoxyethanol (1:1)). The solution was mixed and coated on poly(ethylene terephthalate) film base at a wet thickness of 0.098 mm. It was allowed to dry at 49° C. for 15 minutes. The dye in the film had $\lambda$max at 565 nm, and at 530 nm, the optical density was 1.8 and 0.93, respectively. The film was heated at 160° C. for 10 seconds. The optical density of the heated film was 0.20 at $\lambda$=565 and 0.18 at 530 nm. The reduction in the dye density was 89 percent and 81 percent, at the two wavelengths. The same results were obtained after the film had been held in storage at room temperature for 6 months.

EXAMPLE 3

Synthesis of eicosafluorohbenzopinacol

Perfluorobenzophenone (4.25 g) was dissolved in 30 ml of isopropanol and 220 ml of n-pentane; the ratio of n-pentane/isopropanol being 7.3:1. The solution was purged with nitrogen and irradiated for 2 hours with a Hanovia 450-watt, Hg-arc lamp. The solution, after irradiation, was stored in a refrigerator. A 100 ml volumetric flask was partially filled with the solution and was attached to a rotary vacuum evaporator. The maximum temperature of the water bath was 34° C. The evaporation was carried almost to dryness. The product crystallized during evaporation. It was washed with n-pentane twice. The slurry was centrifuged and decanted. Immediately, the product was dried in air. Pure eicosafluorobenzopinacol was recovered on the basis of IR and mass spectrometric analysis. The yield was 2.12 g or 50 percent. The same synthesis was repeated and yield was 48 percent.

By way of comparison, eicosafluorobenzopinacol cannot be made using a ratio of n-pentane/isopropanol of 40:1.

EXAMPLE 4

Synthesis of decafluorobenzopinacol

Pentafluorobenzophenone (10.4 g) was dissolved in 250 ml of benzene/isopropanol (3.5:1). The solution was purged with nitrogen and irradiated for 6 hours with a Hanovia 450-watt Hg-arc lamp. The solvent was removed using a vacuum evaporator at a temperature less than 40° C. The crystallized product was washed twice with 25 ml of n-pentane. The slurry was centrifuged and n-pentane was decanted. The product was spread on a watch glass and air dried. Recovery of 2,3,4,5,6,2',3',4',5',6'-decafluorobenzopinacol was 9.1 g or 87.5%.

By way of comparison, the yield of this decafluorobenzopinacol is reported in the literature as only 65% when a ratio of non-polar hydrocarbon solvent to alcohol is 40:1.

The invention has been described in detail with particular reference to certain preferred embodiments thereof, but it will be understood that variations and modifications can be effected within the spirit and scope of the invention.

What is claimed is:

1. A process for producing a benzopinacol comprising the steps of, respectively:
   (a) preparing a 0.005 to 1.0 molar neutral or acidic solution of at least one aromatic ketone in a solvent, which is a mixture having a boiling point less than about 120° C., consisting essentially of a non-polar hydrocarbon and an alcohol wherein the volume ratio of said non-polar hydrocarbon to said alcohol is between 3:1 and 8:1;
   (b) irradiating said solution with ultraviolet light at an intensity and for a time sufficient to effect conversion of said aromatic ketone to said benzopinacol; and
   (c) removing said solvent mixture from said solution at a temperature of less than 40° C. sufficient to reduce the rate of benzopinacol decomposition.

2. A process according to claim 1 wherein the solvent mixture of (a) is 0.01 to 0.5 molar in said aromatic ketone.

3. A process according to claim 1 wherein said non-polar hydrocarbon is non-aromatic.

4. A process according to claim 1 wherein said solution is deoxygenated.

5. A process according to claim 1 wherein said alcohol is isopropanol.

6. A process according to claim 1 wherein said benzopinacol is represented by the formula:

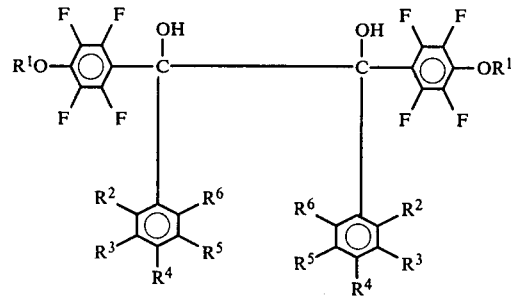

wherein
$R^1$ is hydrogen, alkyl containing 1 to 16 carbon atoms or aryl containing up to 12 carbon atoms;
$R^2$ and $R^6$ independently are selected from the group consisting of hydrogen, halogen or trifluoromethyl;
$R^3$ and $R^5$ independently are selected from the group consisting of hydrogen, halogen and alkyl containing 1 to 16 carbon atoms or, when taken together with $R^4$, represent a tetramethylene group; and $R^4$ is selected from the group consisting of hydrogen, halogen, alkyl containing 1 to 16 carbon atoms, alkoxy containing 1 to 16 carbon atoms and phenoxy;

and when both of the ortho positions of the phenyl groups to which $R^2$ and $R^6$ are attached are substituted, the substituent is fluorine.

7. A process according to claim 1 wherein said benzopinacol is a compound selected from the group consisting of: 4,4″-dimethoxy-2,3,5,6,2″,3″,5″,6″-octafluorobenzopinacol; 4,4′,4″,4‴-tetramethoxy-2,3,5,6,2″,3″,5″,6″-octafluorobenzopinacol; 4,4″-bis(4-methylphenoxy)-2,3,5,6,2″,3″,5″,6″-octafluorobenzopinacol; 4,4″-bis(4-methoxyphenoxy)-2,3,5,6,2″,3″,5″,6″-octafluorobenzopinacol; and 4,4″-diphenoxy-2,3,5,6,2″,3″,5″,6″-octafluorobenzopinacol.

8. A process for producing 4,4″-dimethoxy-2,3,5,6,2″,3″,5″,6″-octafluorobenzopinacol comprising the steps of, respectively:
 (a) preparing a 0.005 to 1.0 molar neutral or acidic solution of 4-methoxy-2,3,5,6-tetrafluorobenzophenone in a solvent, which is a mixture having a boiling point less than about 120° C., consisting essentially of benzene and isopropanol wherein the volume ratio of benzene to isopropanol is between 3:1 and 8:1;
 (b) irradiating said solution with ultraviolet light at an intensity and for a time sufficient to effect conversion of said tetrafluorobenzophenone to said octafluorobenzopinacol; and
 (c) removing said solvent mixture at a temperature of less than 40° C. at which no significant decomposition of said octafluorobenzopinacol occurs.

9. A process for producing eicosafluorobenzopinacol comprising the steps of, respectively:
 (a) preparing a 0.005 to 1.0 molar neutral or acidic solution of perfluorobenzophenone in a solvent, which is a mixture having a boiling point less than 120° C., consisting essentially of n-pentane and isopropanol wherein the ratio of n-pentane to isopropanol is between 3:1 and 8:1;
 (b) irradiating said solution with ultraviolet light at an intensity and for a time sufficient to effect conversion of said perfluorobenzophenone to said eicosafluorobenzopinacol; and
 (c) removing said solvent mixture at a temperature of less than 40° C. at which no significant decomposition of said eicosafluorobenzopinacol occurs.

10. A process for producing 2,3,4,5,6,2′,3′,4′,5′,6′-decafluorobenzopinacol comprising the steps of, respectively:
 (a) preparing a 0.005 to 1.0 molar neutral or acidic solution of pentafluorobenzophenone in a solvent, which is a mixture having a boiling point less than 120° C., consisting essentially of benzene and isopropanol wherein the ratio of benzene to isopropanol is between 3:1 and 8:1;
 (b) irradiating said solution with ultraviolet light at an intensity and for a time sufficient to effect conversion of said pentafluorobenzophenone to said 2,3,4,5,6,2′,3′,4′,5′,6′-decafluorobenzopinacol; and
 (c) removing said solvent mixture at a temperature of less than 40° C. at which no significant decomposition of said 2,3,4,5,6,2′,3′,4′,5′,6′-decafluorobenzopinacol occurs.

* * * * *

UNITED STATES PATENT AND TRADEMARK OFFICE
CERTIFICATE OF CORRECTION

PATENT NO. : 4,168,218
DATED : September 18, 1979
INVENTOR(S) : Jonas Dedinas

It is certified that error appears in the above-identified patent and that said Letters Patent are hereby corrected as shown below:

Column 4, line 1, "$R^2$ and $R^6$" should read ---$R^2$ through $R^6$---.

Column 5, line 20, after "boiling" delete "product" and insert ---point---.

Column 6, line 35, that part of the formula reading " $4,4'$ " should read --- $4,4''$ ---.

Column 7, line 40, "eicosafluorohbenzopinacol" should read --- eicosafluorobenzopinacol ---.

Signed and Sealed this

Twenty-fifth Day of December 1979

[SEAL]

Attest:

SIDNEY A. DIAMOND

Attesting Officer

Commissioner of Patents and Trademarks